(12) United States Patent
Butterworth

(10) Patent No.: US 6,213,124 B1
(45) Date of Patent: *Apr. 10, 2001

(54) SURGICAL DRAPE WITH A SEALABLE POUCH

(75) Inventor: David E. Butterworth, Colleyville, TX (US)

(73) Assignee: Johnson & Johnson Medical, Inc., Arlington, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 08/258,643

(22) Filed: Jun. 13, 1994

Related U.S. Application Data

(63) Continuation-in-part of application No. 08/052,257, filed on Apr. 23, 1993, now Pat. No. 5,345,946.

(51) Int. Cl.[7] .......................... A61B 19/08; A61B 19/00
(52) U.S. Cl. .............................. 128/853; 128/849
(58) Field of Search ................... 128/849–856, 128/DIG. 24; 383/33, 63, 65

(56) References Cited

U.S. PATENT DOCUMENTS

| | | | |
|---|---|---|---|
| 3,386,444 | * 6/1968 | Brenner et al. | |
| 3,416,585 | * 12/1968 | Staller | 383/65 |
| 4,024,862 | 5/1977 | Collins | 128/132 D |
| 4,316,455 | 2/1982 | Stoneback | 128/132 D |
| 4,476,860 | * 10/1984 | Collins et al. | |
| 4,489,720 | * 12/1984 | Morris et al. | 128/853 |
| 4,559,937 | * 12/1985 | Vinson | |
| 4,869,271 | * 9/1989 | Idris | 128/849 |
| 5,038,798 | * 8/1991 | Dowdy et al. | 128/852 |
| 5,148,940 | * 9/1992 | Mendise | 128/849 |
| 5,161,544 | * 11/1992 | Morris | 128/849 |
| 5,339,831 | * 8/1994 | Thompson | 128/852 |
| 5,345,946 | * 9/1994 | Butterworth et al. | 128/853 |

FOREIGN PATENT DOCUMENTS 2 182 375    12/1973   (FR).

OTHER PUBLICATIONS

EPO Search Report for EP 94 30 2896, a corresponding foreign application.

* cited by examiner

Primary Examiner—Michael O'Neill

(57) ABSTRACT

A surgical drape includes a sealable pouch to collect run-off from a surgical site. The pouch is open to receive fluid during a surgical procedure. When the procedure is completed, the pouch is sealed to prevent leakage of the fluid and to permit safe disposal of the contaminated drape. Preferably, the pouch is sealed with an interlocking ridge-and-channel structure of the type commonly used in food and sandwich bags.

3 Claims, 5 Drawing Sheets

SURGICAL DRAPE WITH A SEALABLE POUCH

This application is a continuation-in-part of application Ser. No. 08/052,257, filed Apr. 23, 1993 and issued as U.S. Pat. No. 5,345,946 on Sep. 13, 1994.

BACKGROUND OF THE INVENTION

1. Field of the Invention

This invention relates to surgical drapes; more particularly, to a drape that includes a sealable pouch to collect runoff from a surgical site.

2. Description of the Related Art

Surgical procedures often result in blood and other fluids being produced in the surgical site either directly from the patient or from irrigation fluids used to flush the site. A simple way to control these fluids is to provide towels, or other absorptive materials, in and around the surgical site. When the surgical procedure is expected to involve more fluid run-off than can be absorbed in this way, one or more pouches can be attached to the drape and/or be an integral part of the drape as it is made.

A number of patents have disclosed pouches that are designed to contain run-off generated during surgery.

U.S. Pat. No. 3,386,444, issued on Jun. 4, 1968, to O. R. Brenner et al., discloses a surgical drain bag for receiving bodily fluid draining from a patient during surgery. The bag includes an outlet opening at the bottom and a tubular drain coupling secured into the opening, through which fluid can be removed from the bag.

U.S. Pat. No. 4,476,860, issued on Oct. 16, 1984, to R. F. Collins et al., discloses a drape comprising a main sheet that has adhered to its top surface (away from the patient) a transparent sheet, which includes pockets for holding instruments and collecting body fluids, and a reinforcement sheet. A fenestration extends through the main sheet, transparent sheet, and reinforcement sheet. Body fluids that collect in the pockets are pumped out during surgery with an aspirator.

U.S. Pat. No. 4,559,937, issued on Dec. 24, 1985, to K. D. Vinson (see also U.S. Pat. No. 4,598,458 to McAllester), discloses a fluid collection bag attached to a surgical drape that is used for craniotomy surgical procedures. A slit in the bag permits a suction tube to be introduced into the bag for suctioning fluid out of the bag.

U.S. Pat. No. 4,890,628, issued on Jan. 2, 1990, to E. M. Jackson, discloses a surgical drape with attached fluid collection bag. A drainage opening at the bottom of the bag is fitted with a drain nozzle. The nozzle may be fitted with flexible tubing to continuously drain fluid into a bucket. A shutoff valve in the nozzle or tubing can control fluid release from the bag.

U.S. Pat. No. 5,038,798, issued on Aug. 13, 1991, to R. C. Dowdy et al., discloses an ophthalmic drape that includes a fluid collection pouch that substantially surrounds the surgical site on three sides. There is no disclosure regarding emptying the pouch.

Surgical drapes that include fluid-collection pouches near a fenestration for collecting fluids generated during surgery are also available commercially. Suppliers of such drapes are, for example, Neuromedics, Inc., Sugar Land, Tex. and Alcon Surgical, Fort Worth, Tex.

Although others have addressed the issue of collecting fluid that emanates from a surgical site, their fluid collection pouches have no provision for closing them after use to prevent leakage.

SUMMARY OF THE INVENTION

In accordance with the present invention, a surgical drape comprises a) a sheet for placement over a patient and comprising
   i) a bottom surface for contacting the patient,
   ii) a top surface for facing away from the patient after placement, and
   iii) a fenestration; and
b) a pouch on the top surface of the sheet, near the fenestration, for collecting fluid runoff during surgery, the pouch comprising
   i) a top edge and bottom edge joined by two opposing side edges, the side edges and bottom edge being sealed closed, and
   ii) means for detachably sealing the top edge to permit opening the pouch to receive fluid and then closing the pouch to prevent leakage of the fluid.

In another embodiment of the present invention, a surgical drape comprises a) a sheet for placement over a patient and comprising
   i) a bottom surface for contacting the patient,
   ii) a top surface for facing away from the patient after placement, and
   iii) a fenestration; and
b) a pouch on the top surface of the sheet, near the fenestration, for collecting fluid runoff during surgery, the pouch comprising
   i) a thermoplastic layer having an outer perimetric edge and an opening defined by an inner perimetric edge, the outer perimetric edge being secured to the top surface of the sheet in a liquid tight seal along a line that completely surrounds the fenestration, and
   ii) means for detachably sealing the inner perimetric edge to the top surface of the sheet to permit opening the pouch to receive fluid and then closing the pouch to prevent leakage of the fluid.

By including a sealing means on the fluid-collecting pouch, the drape of the present invention facilitates safe disposal after the drape is used in a surgical procedure during which substantial amounts of fluid are generated. Furthermore, there is no need to drain the fluid from the pouch before disposing of the drape.

DETAILED DESCRIPTION OF THE INVENTION

Surgical drapes isolate the operative site to maintain sterility and to prevent contamination. Blood and other body fluids that are generated during surgery can often be absorbed by towels or other absorbent materials surrounding the surgical site. However, in surgical procedures that generate substantial quantities of fluids in the surgical site—body and/or irrigating fluids—it is necessary to collect and contain these fluids safely. In particular, it is essential to avoid contacting healthcare workers with fluids that are potentially harmful. Fluid collection bags have been used in surgical procedures in conjunction with surgical drapes to collect these fluids. As for disposing of the fluids, in some cases, they are removed by suction or aspiration during the procedure. In other cases, a drain plug is opened at the end of the procedure to drain the fluid into a disposal container. In either case, disposing of the fluid requires additional devices, containers, and procedures that are at a minimum inconvenient and that may add to the danger of contamination.

The present drape provides an easier way to deal with the contaminated fluid that accumulates in a pouch during surgery. The pouch is simply sealed and is then disposed of, together with the attached drape, as contaminated ("red-bag") waste.

Figure 1:
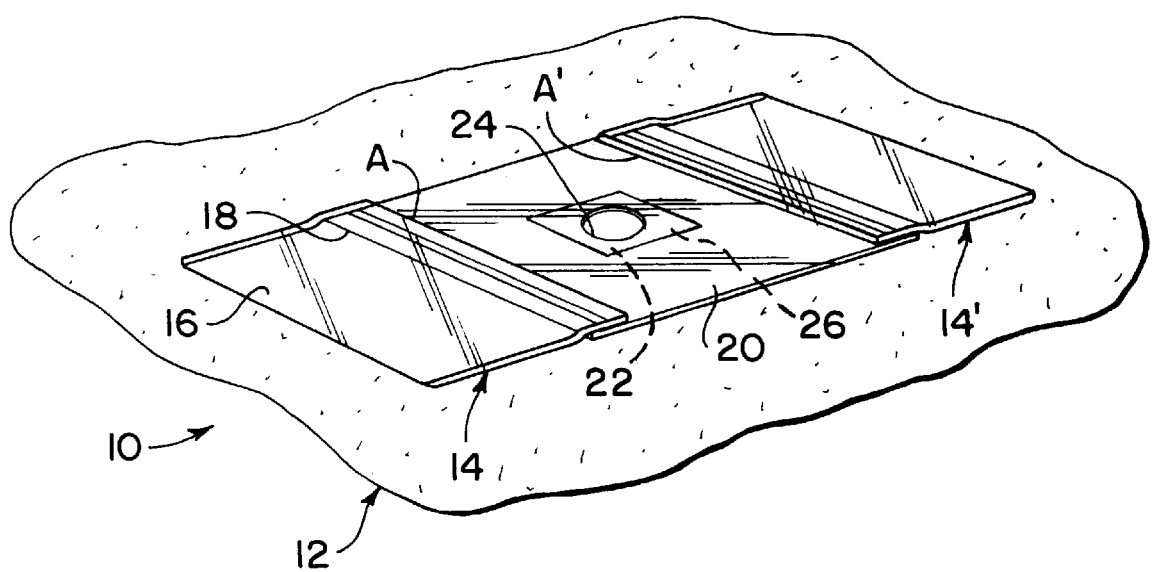
FIG. 1 is a perspective view of the region in the vicinity of the fenestration of a surgical drape of the present invention.
Figure 3:
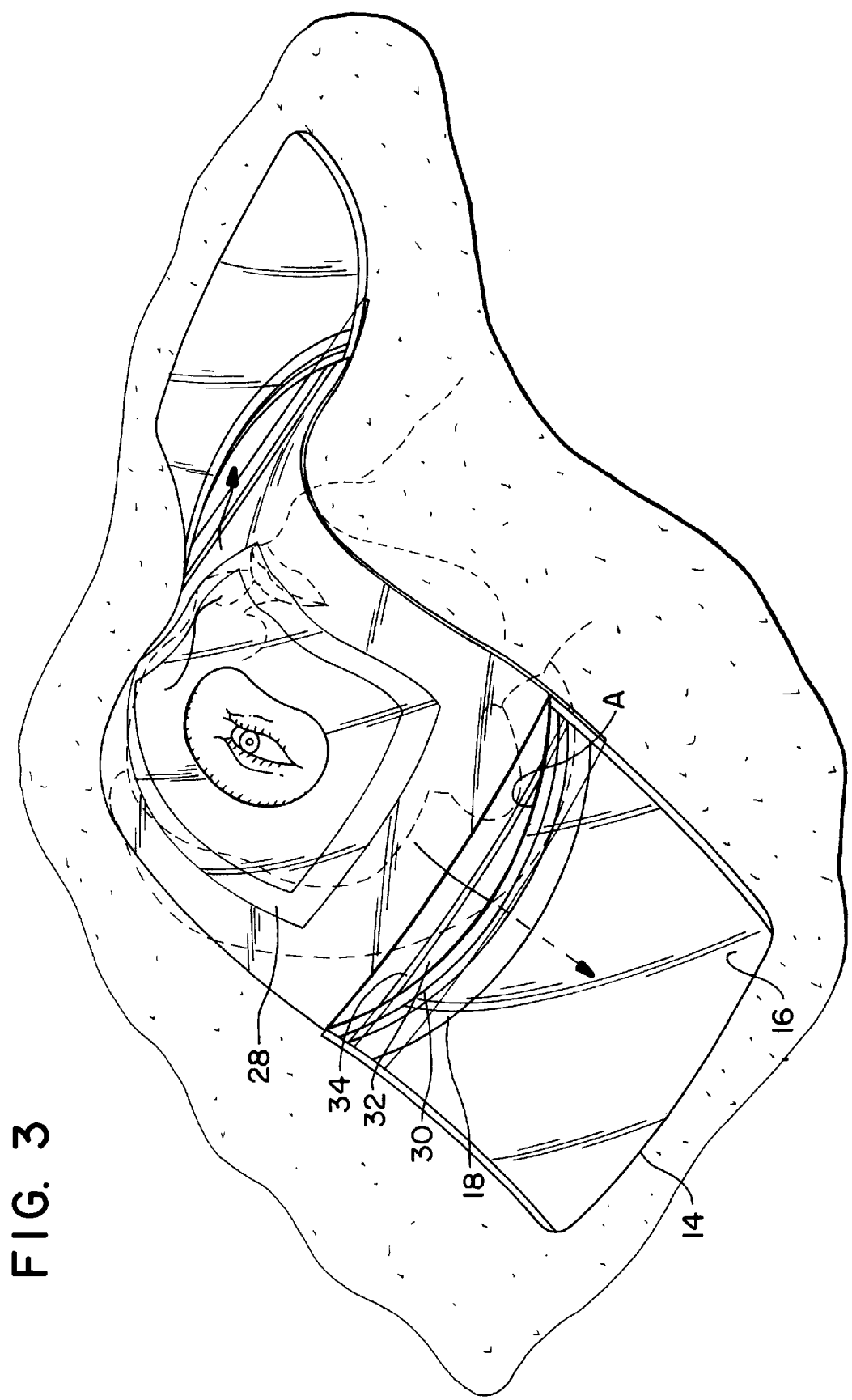
FIG. 3 is a perspective view of an ophthalmic drape of the present invention.

FIG. 1 is a perspective view of a drape of the present invention adapted for surgical procedures that generate large quantities of fluid, which may include blood, other body fluids, irrigation fluid, etc. Only the region in the vicinity of the fenestration is shown. The drape 10 includes a sheet 12 and pouches 14 and 14'. The pouches are generally attached to sheet 12 along the edge that is proximal to the fenestration, but they could be attached over their entire bottom surface. Conventional attachment means—adhesive, tape, or heat sealing, four example—may be used. Although two pouches are shown in FIG. 1, it is clear that additional pouches could be attached to sheet 12 in order to surround the fenestration more completely. Alternatively, only a single pouch may be used, and pouch elements are generally discussed above and below with respect to pouch 14 alone. The top panel 16 of pouch 14 has an optional bendable strip 18 near unsealed edge A. As shown in FIG. 3, the strip may be bent so as to maintain the pouch in the open position in order to collect fluids during the surgery. Sheet 12 is preferably a nonwoven fabric, e.g., spunlaced or meltblown, or a clear thermoplastic film such as polyethylene or polyurethane. Pouch 14 is a fluid-impervious, flexible thermoplastic material that is preferably transparent. When sheet 12 comprises a liquid impervious material, then the sheet itself can provide one face of pouch 14, with a second layer 16 of liquid impervious material attached to it in a liquid tight seal along all the edges except top edge A, through which the fluid enters.

Optional reinforcement section 20 is adhered to sheet 12. Depending on the procedure and the surgeon's preferences, section 20 may be absorbent, undesirably adding to stiffness, or a clear thermoplastic film. Fenestration 24 may be cut during the manufacturing process or, alternatively, it may be cut by a healthcare worker in preparation for surgery. Fenestration 24 in optional reinforcement section 20 is smaller than fenestration 22 in sheet 12, and the underside of reinforcement section 20 is optionally coated with adhesive 26 to adhere to the patient's skin in the area surrounding the surgical site. Optional reinforcement section 20 is preferably a fluid-impervious thermoplastic sheet that is laminated or otherwise adhered to sheet 12 and facilitates the flow of fluid to pouches 14 and 14', while preventing strikethrough. Alternatively, a single sheet may form both reinforcement section 20 and pouch 14, with the pouch being formed by folding over upon itself the section edge that is distal from the fenestration and then sealing two side edges (e.g., by heat or adhesive) to form the pouch. When reinforcement section 20 is not present, fenestration 24 is simply cut into sheet 12.

Figure 2:
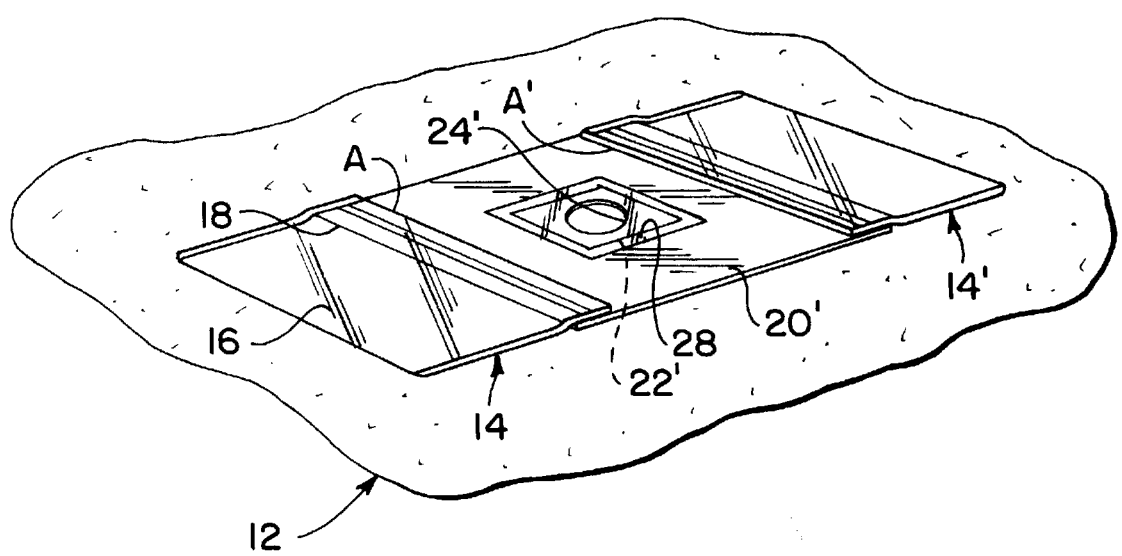
FIG. 2 depicts a slightly different embodiment of the drape of FIG. 1.

FIG. 2 depicts an alternative embodiment in which an incise section 28 is adhered to optional reinforcement section 20'. If reinforcement section 20' were absent, incise section 28 could be adhered directly to sheet 12. Incise section 28 is adhered to its underlying support in the region surrounding fenestration 22' and has cut into it fenestration 24'. Fenestration 24' may be cut during the manufacturing process or in preparation for surgery. Incise section 28 comprises a very thin and flexible sheet of thermoplastic film with an adhesive that attaches to the patient's body with an adhesive that does not irritate the skin. Incise section 28 is preferably a polyethylene sheet coated with a hypoallergenic adhesive. It is not needed, but it is preferred. In the absence of incise section 28 (i.e., in the embodiment of FIG. 1), if reinforcement section 20 is to be adhered to the skin of the patient undergoing surgery, it must have two types of adhesive on its bottom side. Surrounding fenestration 24 and within the perimeter of fenestration 22, must be an adhesive 26 that does not irritate the patient's skin. Further from fenestration 24 reinforcement section 20 has another adhesive, generally not adapted for use on skin, to adhere it to sheet 12.

FIG. 3 is a perspective view of a drape 10 of this invention in place on a patient. Although the drape shown is an ophthalmic drape, it is clear that this type of drape, appropriately modified, can be used for a variety of procedures. Top panel 16 of pouch 14 has a raised ridge 30 that extends outward from its surface near, and parallel to, edge A. Bottom panel 32 of pouch 14 has a channel structure 34 positioned so that it can engage raised ridge 30, thereby sealing pouch 14 when top panel 16 is pushed against bottom panel 32. This interlocking sealing mechanism, similar to the mechanism disclosed in U.S. Pat. No. 4,186,786, issued Feb. 5, 1980, to G. F. Kirkpatrick, is commonly used in food and sandwich bags and is identified by the "Ziploc*" mark. Although a single interlocking ridge/channel structure is shown, multiple structures would provide a more secure closure. The sealing mechanism is depicted in cross section in FIG. 5. Other means for sealing pouch 14 may be used in place of the Ziploc* mechanism depicted in FIG. 3. Among these other means are fluid-tight hook and loop ("Velcro*") fasteners and wet stick adhesives, for example.

Figure 4:
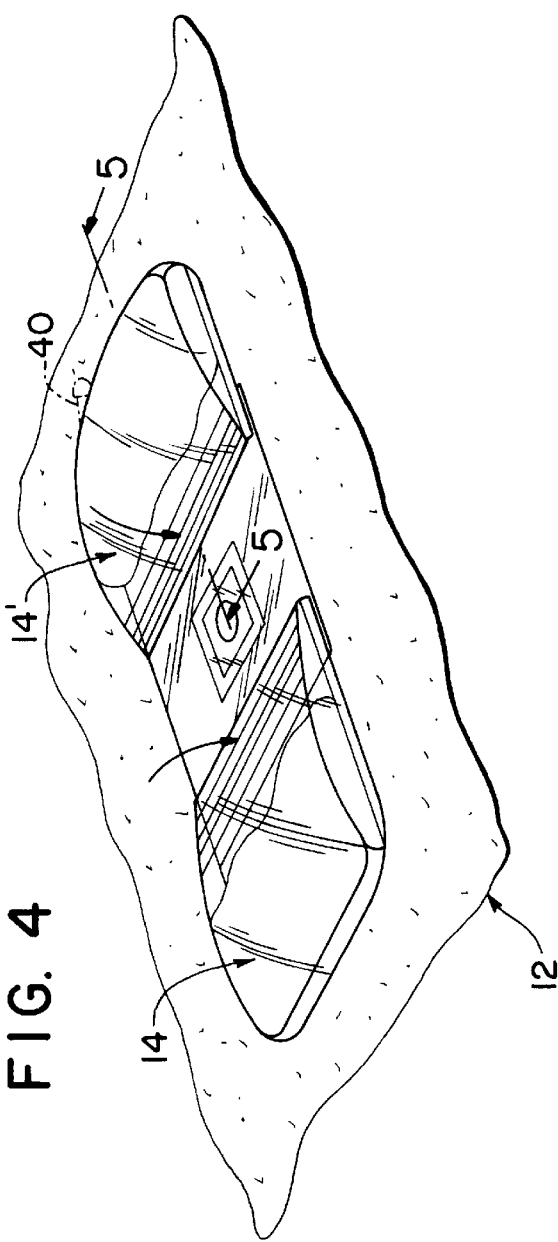
FIG. 4 is a perspective view of the drape of FIG. 3 after the surgical procedure has been completed and the pouches have been sealed.

FIG. 4 is a perspective view, which shows that pouches 14 and 14' are sealed after the surgery is complete. Sheet 12, with attached pouches 14 and 14' can then be disposed of (as red-bag waste) without the need to first drain fluid from the pouches. FIG. 4 also shows a phantom optional sealable drain port 40, which permits fluid to be drained from the pouch.

Figure 5:
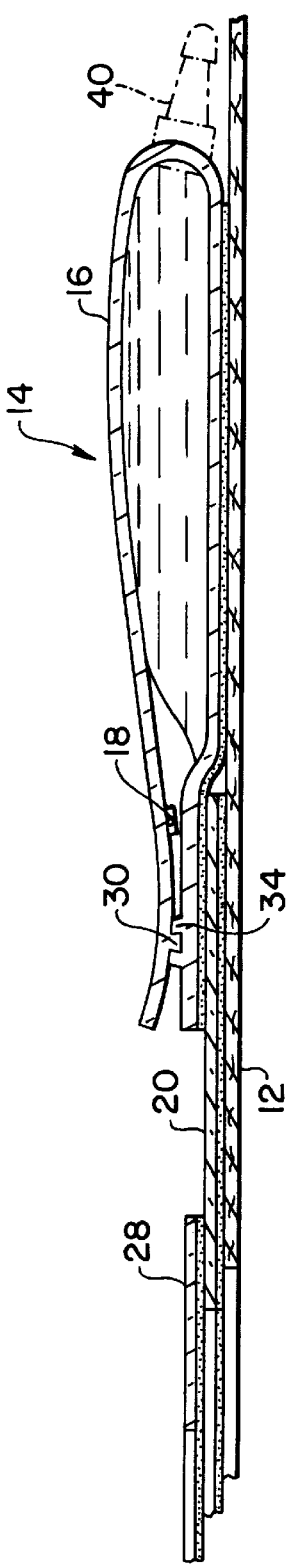
FIG. 5 is a cross section through the drape as taken along line 5—5 of FIG. 4.

FIG. 5 is a cross section through the sheet of FIG. 4.

Figure 6:
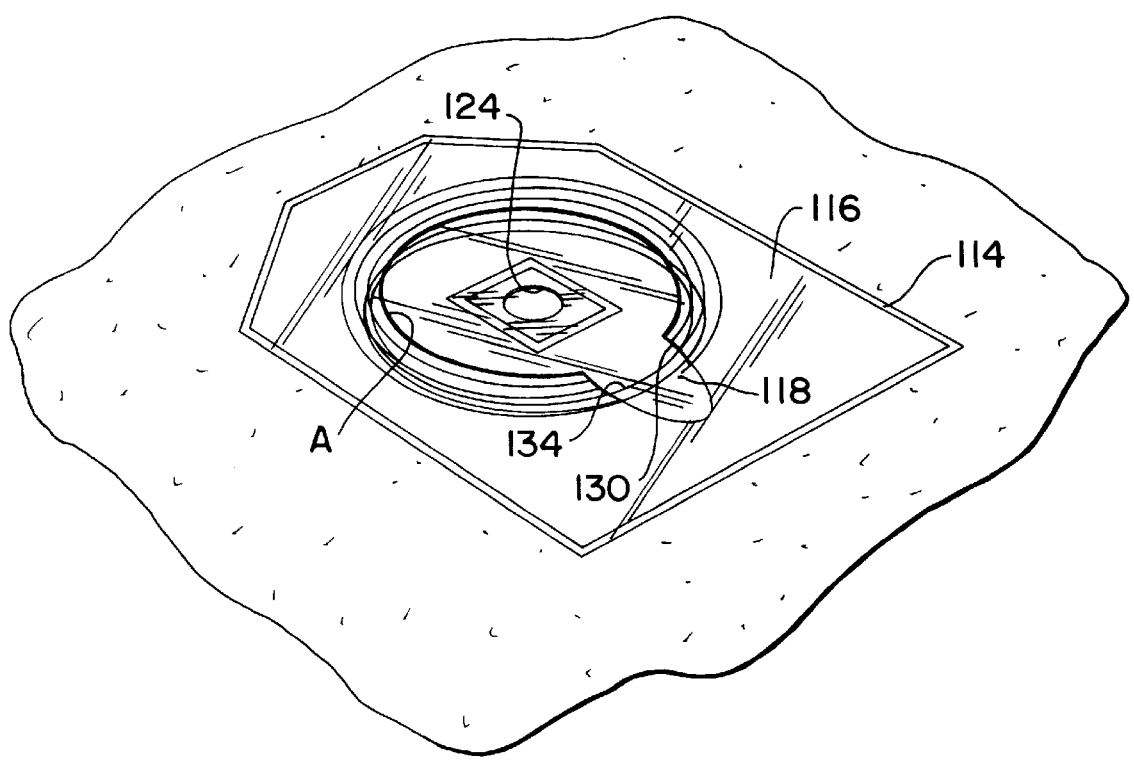
FIG. 6 is a perspective view, in partial cutaway, of another embodiment of the present invention.

FIG. 6 depicts another embodiment of the present invention, which provides fluid control completely surrounding fenestration 124. During a surgical procedure, bendable strip 118 retains the circular opening A of pouch 114 in a raised position that permits fluid to drain into the pouch. After the procedure has been completed, raised ridge 130 that extends from the top panel 116 is pressed into sealing engagement with channel 134 to seal pouch 114 for disposal. Drapes that provide fluid control over a full 360° circumference around a fenestration, as provided by the structure of FIG. 6, are described in U.S. Pat. No. 5,161,544, issued on Nov. 10, 1992, to H. K. Morris, and that description is included herein by reference.

While this invention has been described in conjunction with certain specific embodiments thereof, it is evident that many alternatives, modifications, and variations will be apparent to those skilled in the art, in light of the above description. Accordingly, it is intended to embrace all such embodiments that fall within the spirit and broad scope of the appended claims.

What is claimed is:

1. A disposable surgical drape, comprising
    a) a sheet for placement over a patient and comprising
        i) a bottom surface for contacting the patient,
        ii) a top surface for facing away from the patient after placement,
    and
        iii) a fenestration; and
    b) a pouch on the the sheet, near the fenestration, for collecting fluid runoff during surgery, the pouch comprising
        i) a thermoplastic layer having an outer perimetric edge and an opening defined by an inner perimetric edge, the outer perimetric edge being secured to the sheet in a liquid tight seal along a line that completely surrounds the fenestration, and
        ii) closure means for sealing the inner perimetric edge to the sheet to close the pouch in a fluid tight manner to prevent leakage of the fluid therefrom.

2. The surgical drape of claim 1 further comprising a bendable strip extending substantially around the inner perimetric edge of the thermoplastic layer, whereby the strip retains the inner perimetric edge in a defined shape above the sheet.

3. The surgical drape of claim 1 in which the closure means is an interlocking ridge-and-channel structure.

* * * * *